United States Patent [19] [11] 4,439,198
Brightman, II et al. [45] Mar. 27, 1984

[54] BIODEGRADABLE OCULAR INSERT FOR CONTROLLED DELIVERY OF OPHTHALMIC MEDICATION

[75] Inventors: Alan H. Brightman, II; Michael C. Theodorakis, both of Champaign, Ill.

[73] Assignee: University of Illinois Foundation, Urbana, Ill.

[21] Appl. No.: 281,911

[22] Filed: Jul. 9, 1981

[51] Int. Cl.³ .............................................. A61M 7/00
[52] U.S. Cl. .................................... 604/894; 604/893
[58] Field of Search ................ 128/260, 130; 604/893, 604/894; 424/19–25

[56] References Cited

U.S. PATENT DOCUMENTS 3,598,115 8/1971 Horne .................................. 128/130
4,186,184 1/1980 Zaffaroni ............................ 128/260
4,201,210 5/1980 Hughes et al. ...................... 128/260

Primary Examiner—Richard J. Apley
Assistant Examiner—T. J. Wallen
Attorney, Agent, or Firm—Mathew L. Kalinowski

[57] ABSTRACT

An ocular insert is disclosed that is attachable to the third eyelid of animals to provide controlled delivery of ophthalmic medication. The insert includes a disc impregnated with medication in controlled-release form and a biodegradable spear for attachment of the insert to the third eyelid. An insert effective for treatment of infectious bovine keratoconjunctivitis comprises a disc impregnated with chloramphenicol sodium monosuccinate and a spear of biodegradable polylactic acid which provides for retention of the insert in the eye, and consequent medication, for up to seven days.

4 Claims, 2 Drawing Figures

BIODEGRADABLE OCULAR INSERT FOR CONTROLLED DELIVERY OF OPHTHALMIC MEDICATION

This invention was made in the course of research work funded by a grant from the Illinois State Department of Agriculture.

This invention relates to an ocular insert attachable to the third eyelid of animals that provides controlled delivery of ophthalmic medication to the eye. More specifically, this invention relates to an ocular insert impregnated with medication in controlled-delivery form and having a biodegradable spear which provides for attachment of the insert to the third eyelid and for subsequent release of the insert.

It is well recognized in the art that drug delivery systems that provide a steady sustained release offer therapeutic advantages over conventional solutions and ointments. For example, U.S. Pat. No. 3,887,699 discloses a biodegradable polymeric article impregnated with controlled release drugs for subcutaneous implantation for controlled release of medication into the bloodstream. Although effective for a variety of purposes, such implants are inefficient and only moderately, if at all, effective for the treatment of obstinate eye infections, such as bovine keratoconjunctivitis (pinkeye) because of poor transfer of drug from the bloodstream to ocular fluids. Furthermore, high levels of drugs in the bloodstream of cattle so treated are undesirable because of possible residual contamination of milk and meat.

In recent years significant advances have been made in the field of ophthalmic drug delivery systems. For example, U.S. Pat. No. 3,416,530 entitled "Eyeball Medication Dispensing Tablet" and U.S. Pat. No. 3,618,604 entitled "Ocular Insert" disclose a drug dispensing ocular insert which releases controlled amounts of drug to the eye. Such ocular inserts are fabricated of materials that are biologically inert, non-allergenic, and non-biodegradable in tear fluid. The ocular inserts are adapted for insertion in the cul-de-sac of the conjunctiva between the sclera of the eyeball and the lower lid, and are held in place against the eyeball by the pressure of the lid. On termination of the therapeutic program the ocular insert is removed from the eye.

While the above-described ocular inserts have proved to be markedly superior to the prior art ointments and liquids, a disadvantage is that the insert remains intact during the course of therapy and must be removed on termination of treatment, which can present difficulties and additional time-consuming treating costs. To eliminate this disadvantage, ocular inserts that are biodegradable in the environment of the eye are disclosed in U.S. Pat. Nos. 3,867,519; 3,960,150; and 3,962,414. Such inserts biodegrade into innocuous products concurrently with the dispensing of the drug and thus do not have to be removed at the end of the therapeutic program.

The above-listed patents are incorporated herein by reference and are cited as illustrative of the state of the art. All of the ocular inserts disclosed are adapted for insertion in the cul-de-sac of the conjunctiva between the sclera of the eyeball and the lower lid. Such insertion is suitable for treatment of the human eye but is unsuitable for the treatment of the eyes of farm animals whose eyes possess a nictitating membrane or third eyelid. A primary function of the third eyelid is to remove foreign objects from the eye; therefore the ocular inserts described above would be rejected immediately after insertion, or at best after an extremely short retention period.

Accordingly, it is an object of this invention to provide an ocular insert for mammalian animals possessing a third eyelid that does not suffer from the disadvantages of prior-art devices.

It is another object of this invention to provide an ocular insert that is attachable to the third eyelid with biodegradable attachment means.

Still another object of this invention is to provide an ocular insert that is attachable to the third eyelid of cattle and provides effective treatment of bovine keratoconjunctivitis (pinkeye).

These and other objects will become apparent as description of the invention proceeds.

In accordance with this invention an ocular insert is provided that is adapted for attachment to the third eyelid of mammalian animals and that includes a reservoir containing an ophthalmic drug in amount and form to provide continuous, controlled administration of a predetermined therapeutically effective dosage of the drug to the eye over a prolonged period of time; and a biodegradable spear protruding from the reservoir for piercing the third eyelid and attaching the insert thereto.

The reservoir can be in the form of a disc or pledget fabricated from materials that are non-toxic, non-allergenic, and non-irritating to the eye. Suitable materials are polymeric compositions, for example polyolefins such as polyethylene and polypropylene; polyamides; and polyesters such as polyethylene terephthalate, polyacrylates, and the like. Preferably, biodegradable polymeric compositions are employed, for example polylactic acid, polylactic glyconic acid, polysaccharide derivatives, polyaminoacids, cellulose derivatives such as ethyl cellulose, and the like.

The ophthalmic drug is incorporated in the reservoir by known, conventional means. For example, the drug can be dispersed intimately within the polymeric material constituting the reservoir in soluble or partly soluble form to provide slow release into the eye by diffusion or dissolution in the tear fluid. Alternatively, the reservoir can contain microcapsules or a central core in which the drug is surrounded by a release-controlling coating such as ethylene vinylacetate which is soluble and/or biodegradable in tear fluid. These and other methods of controlled release of medication are described by Gelatt, K. N. et al., Am. J. Vet. Res. 40, No. 5, 702-4 (1979), which reference is cited as illustrative of the state of the art.

The spear for attaching the reservoir to the third eyelid is fabricated from biodegradable polymeric material such as, for example, polylactic acid, polylactic glyconic acid, polysaccharide derivatives, polyaminoacids, cellulose derivatives such as ethyl cellulose, and the like. The spear is made of length such that it penetrates the third eyelid thereby securely holding the drug-containing reservoir in the eye. The material for and the thickness of the spear are pre-determined to provide a predictable rate of biodegradation, controlled duration of retention of the reservoir, and thus controlled duration of therapeutic treatment. The spear can be fabricated as an integral unit with the reservoir or it can be fabricated separately and fastened to the reservoir by suitable means, for example, with an adhesive.

DESCRIPTION OF THE PREFERRED EMBODIMENTS

The invention is further illustrated by reference to the following examples and procedures.

An ocular insert suitable for treating pinkeye in cattle was made as follows. Dissolved in 100 ml of methylene chloride were 0.8 g of chloramphenicol sodium monosuccinate, 0.1 g of tributyl citrate, and 2.0 g of polylactic acid (mol. wt. 50,000–60,000). The solution was evaporated to dryness, the residue was wrapped in aluminum foil, and then melt-pressed at 170° C. for 30 seconds under a load of 3 metric tons to produce a translucent film having a uniform thickness of 1.5 mm. Oval discs 10 mm by 20 mm were cut from the film. In a similar manner, discs can be made impregnated with the drug oxytetracycline hydrochloride.

Figure 1:
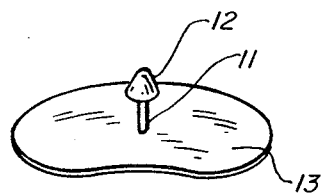
FIG. 1 is a perspective view of the ocular insert.

Spears for attachment to the discs were fashioned from polylactic acid powder (mol. wt. 50,000–60,000). The powder was placed in a die in the form of a spear in which the shaft of the spear was about 4 mm in length and about 1.5 mm in diameter, and in which the barb at the end of the spear was of conical shape about 3 mm in length and about 3 mm in diameter at the base. The die containing polylactic acid powder was heated to 100° C. under a pressure of 2 tons/square inch for 15 seconds to form the spear. The spear was attached to the medicated disc with polycyanoacrylate adhesive. As shown in FIG. 1, the spear shaft 11 having a barbed end 12 is attached to disc 13 which serves as a reservoir for the ophthalmic drug.

Figure 2:
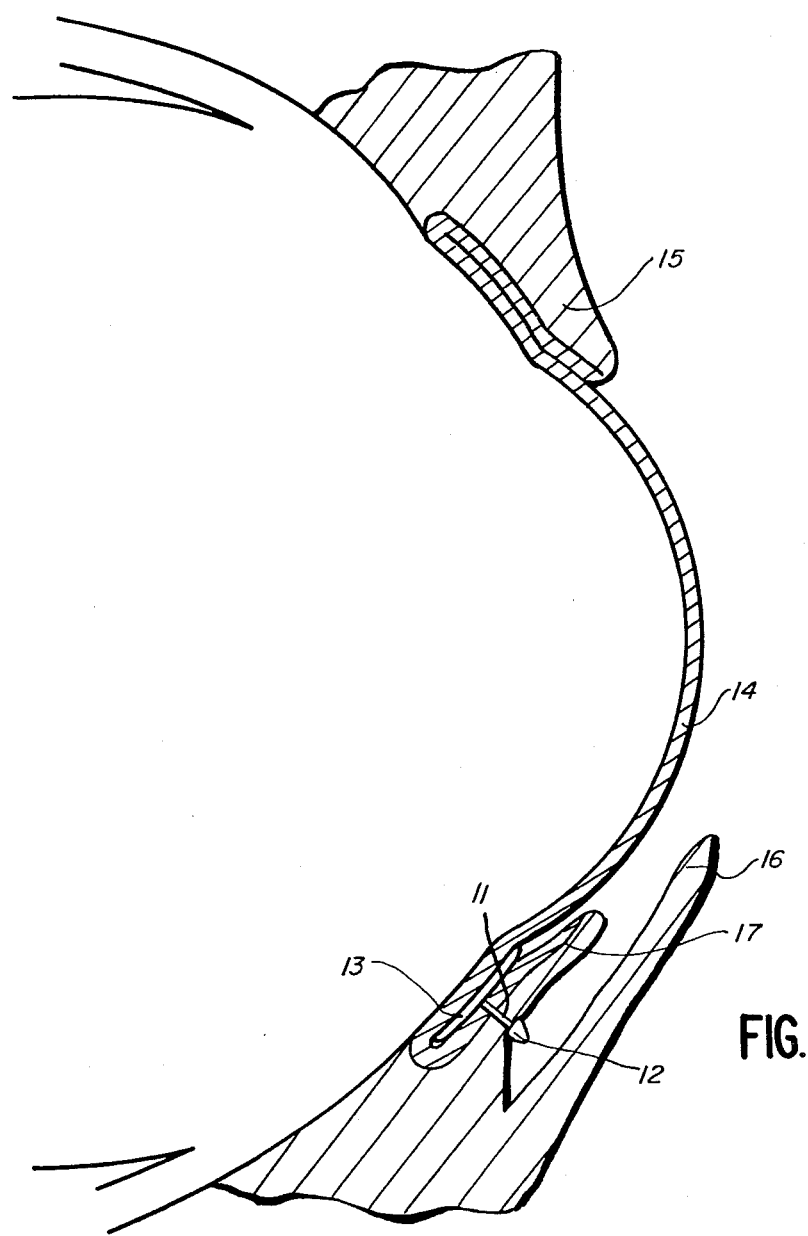
FIG. 2 illustrates placement of the ocular insert in the nictitating membrane of the eye.

In a therapeutic program, the insert was attached to the third eyelid of a cow as illustrated in FIG. 2. In the cross-section of the eye in FIG. 2, the cornea is shown at 14, the upper eyelid at 15, the lower eyelid at 16, and the third eyelid at 17. The third eyelid 17 is shown pierced by barbed end 12 and shaft 11 of the spear thereby placing disc 13 impregnated with chloramphenicol sodium monosuccinate in contact with the cornea 14. The insert was retained in the eye for seven days during which slow release of drug into the tear fluid provided treatment of pinkeye. Upon biodegradation of the spear at the end of seven days, the residual disc was flipped from the eye, thereby terminating treatment.

The ocular disc can be placed with the medicated reservoir on either side of the third eyelid. In either case, medication is dispensed to the tear fluid in amount and duration effective for treatment of pinkeye.

It is clear from the foregoing disclosure that the ocular insert of this invention provides means for controlling both the amount and duration of medication. Use of the insert in the treatment of pinkeye and other eye diseases in animals possessing a third eyelid is therapeutically effective, and in addition offers significant advantages over conventional, repetitive treatments with ointments and solutions.

Although this invention has been described with particular reference to certain preferred embodiments thereof, it is understood that modifications and variations can be effected within the spirit and scope of the appended claims. It is intended that all material contained in the above description and figures shall be interpreted in an illustrative and not in a limiting sense.

What is claimed is:

1. An ocular insert adapted for attachment to the third eyelid of a mammalian animal comprising a substantially disc-shaped reservoir impregnated with an ophthalmic drug in amount and form to provide continuous, controlled administration of a pre-determined, therapeutically effective dosage of drug to the eye over a prolonged period of time; and a fixed spear of biodegradable material protruding from the reservoir for piercing the third eyelid and attaching the insert thereto, said biodegradable material being selected from the group consisting of polylactic acid, polylactic glyconic acid, polysaccharide derivatives, polyaminoacids, cellulose, and ethyl cellulose.

2. The ocular insert of claim 1 wherein the reservoir consists essentially of an organic polymer selected from the group consisting of polyolefins, polyesters, polylactic acid, polylactic glyconic acid, polysaccharide derivatives, polyaminoacids, cellulose, and ethyl cellulose, said organic polymer being impregnated with a therapeutically effective amount of an ophthalmic drug.

3. The ocular insert of claim 1 wherein both the reservoir and the spear comprise polylactic acid having a molecular weight of from about 50,000 to about 60,000.

4. The ocular insert of claim 3 wherein the ophthalmic drug is selected from the group consisting of chloramphenicol and oxytetracycline hydrochloride.

* * * * *